United States Patent
Wood

(10) Patent No.: US 9,554,980 B2
(45) Date of Patent: Jan. 31, 2017

(54) COMPOSITION AND PROCESS FOR PERMANENT SHAPING OF HUMAN HAIR

(75) Inventor: Jonathan Wood, Weinheim (DE)

(73) Assignee: KAO Germany GmBH, Darmstadt (DE)

( * ) Notice: Subject to any disclaimer, the term of this patent is extended or adjusted under 35 U.S.C. 154(b) by 0 days.

(21) Appl. No.: 13/993,500

(22) PCT Filed: Dec. 23, 2011

(86) PCT No.: PCT/EP2011/073923
§ 371 (c)(1),
(2), (4) Date: Jun. 12, 2013

(87) PCT Pub. No.: WO2012/089650
PCT Pub. Date: Jul. 5, 2012

(65) Prior Publication Data
US 2013/0276809 A1   Oct. 24, 2013

(30) Foreign Application Priority Data
Dec. 27, 2010   (EP) .................... 10016086

(51) Int. Cl.
*A61Q 5/04* (2006.01)
*A61Q 5/10* (2006.01)
*A61K 8/81* (2006.01)

(52) U.S. Cl.
CPC .............. *A61K 8/8182* (2013.01); *A61Q 5/04* (2013.01); *A61Q 5/10* (2013.01); *A61K 2800/88* (2013.01)

(58) Field of Classification Search
None
See application file for complete search history.

(56) References Cited

U.S. PATENT DOCUMENTS

| | | | |
|---|---|---|---|
| 4,214,596 A | | 7/1980 | Davis et al. |
| 2002/0187117 A1* | | 12/2002 | Devin-Baudoin et al. .. 424/70.2 |
| 2005/0241076 A1* | | 11/2005 | Bureiko ............ A61K 8/8152 8/405 |
| 2008/0025938 A1* | | 1/2008 | Cassier ................. 424/70.5 |
| 2008/0279804 A1* | | 11/2008 | Parker et al. .......... 424/70.11 |
| 2009/0041700 A1* | | 2/2009 | Molenda et al. ......... 424/70.2 |
| 2009/0258806 A1* | | 10/2009 | Hoffmann et al. ......... 510/122 |
| 2011/0150810 A1* | | 6/2011 | Molenda et al. ......... 424/70.9 |

FOREIGN PATENT DOCUMENTS

| | | |
|---|---|---|
| EP | 2 011 479 A1 | 1/2009 |
| EP | 2 177 245 A1 | 4/2010 |
| EP | 2 196 178 A1 | 6/2010 |

OTHER PUBLICATIONS

Technical Information of Luvigel® advanced ( Dec. 2009).*
International Search Report mailed Jun. 6, 2012.

* cited by examiner

*Primary Examiner* — Jyothsna Venkat
(74) *Attorney, Agent, or Firm* — Norris McLaughlin & Marcus, P.A.

(57) ABSTRACT

Compositions and processes permanent shape human hair for the permanent waving of human hair with an excellent waving effect as well as for the straightening of curled hair. A composition for permanently shaping hair has at least one reducing agent or at least one oxidizing agent and a cross linked copolymer of vinylpyrrolidone, vinylimidazol, 3-methyl-1-vinylimidazolium chloride and methacrylic acid. A process for permanent shaping hair wherein a composition comprising at least one reducing agent is applied and rinsed off from hair after a processing time of 1 to 30 min and at a temperature of 20 to 45° C. and a composition comprising at least one oxidizing agent is applied and processed for 1 to 20 min at a temperature range of 20 to 45° C. and rinsed off from hair wherein at least one of the compositions has a cross linked copolymer.

16 Claims, No Drawings

COMPOSITION AND PROCESS FOR PERMANENT SHAPING OF HUMAN HAIR

This application is a 371 application of PCT/EP2011/073923 filed Dec. 23, 2011, which claims foreign priority benefit under 35 U.S.C. §119 of European Application No. 10016086.0 filed Dec. 27, 2010.

Present invention relates to a composition and a process for permanent shaping of human hair used both for the permanent waving of human hair with an excellent waving effect as well as for the straightening of curled hair.

It is generally known that permanent shaping is carried out according to a two step process. In the first step, the reductive splitting of the cysteine disulfide bonds is achieved by a reducing agent, and in the second step, neutralization is carried out by application of an oxidizing agent, whereby the cysteine disulfide bonds are restored in the new shape.

The reducing agent still most frequently used today is thioglycolic acid, also in form of the salts thereof, in particular its ammonium salt, although numerous other thio compounds have been proposed for this purpose, which, however, mostly did not succeed.

The compositions containing thioglycolates are customarily applied at a pH-value between 7 and 10, in particular 8.5 and 9.5.

It is also known in the art that the compositions used for permanent shaping hair, reducing and oxidizing compositions and also pre-treatment and intermediate treatment compositions, if present, must have certain consistency for achieving optimal results. Some polymers such as hydroxyethyl cellulose have been suggested in number of textbooks. Although this, there is still need for further improvement especially in the area homogeneous straightening and curling hair which comprises previously damaged parts, but very much inhomogeneous in degree of damage in its length.

The present invention starts from the task of providing a process for the permanent shaping of human hair wherein reducing and oxidizing compositions applied onto hair wherein at least one of the reducing and oxidizing compositions comprises a cross linked copolymer of vinylpyrrolidone, vinylimidazol, 3-methyl-1-vinylimidazolium chloride and methacrylic acid. Hair waved or straightened according to the process of the present invention is homogeneously waved or straightened and looks attractive and feels natural upon touching by hand.

Accordingly, the first object of the present invention is a composition for permanently shaping hair comprising at least one reducing agent and a cross linked copolymer of vinylpyrrolidone, vinylimidazol, 3-methyl-1-vinylimidazolium chloride and methacrylic acid.

The second object of the present invention is a composition comprising at least one oxidizing agent at a concentration of 0.1 to 5%, preferably 0.2 to 5% more preferably 0.2 to 3% and most preferably 0.2 to 2% by weight calculated to the total composition and preferably selected from hydrogen peroxide and sodium bromate and a cross linked copolymer of vinylpyrrolidone, vinylimidazol, 3-methyl-1-vinylimidazolium chloride and methacrylic acid.

The third object of the present invention is a process for permanent shaping hair wherein it is optionally washed or wetted or shampooed and a composition comprising at least one reducing agent is applied and rinsed off from hair after a processing time of 1 to 30 min and at a temperature of 20 to 45° C. and a composition comprising at least one oxidizing agent is applied and processed for 1 to 20 min at a temperature range of 20 to 45° C. and rinsed off from hair wherein at least one of the two compositions comprises a cross linked copolymer of vinylpyrrolidone, vinylimidazol, 3-methyl-1-vinylimidazolium chloride and methacrylic acid.

The forth object of the present invention is a process for permanent shaping hair wherein a composition comprising at least one reducing agent is applied and rinsed off from hair after a processing time of 1 to 30 min and at a temperature of 20 to 45° C. and a composition comprising at least one oxidizing agent is applied and processed for 1 to 20 min at a temperature range of 20 to 45° C. and rinsed off from hair wherein both compositions comprise a cross linked copolymer of vinylpyrrolidone, vinylimidazol, 3-methyl-1-vinylimidazolium chloride and methacrylic acid.

In case that the aim of using the process is perming (curling), prior to application of the reducing agent or during the application of the reducing agent, even after the application of the reducing agent, hair is put on the curlers and the curlers are taken off prior to or during or after application of the oxidizing composition or after processing of the oxidizing composition. The selection of the timing when the curlers are put and taken off from hair is very much dependent on the curling efficiency aimed. For stronger curls it is preferred that the curlers are put on the hair before application of the reducing agent. For stronger curls it is preferred that the curlers are taken off at the end of the processing time of oxidizing agent, and for relatively weaker, slight curling effect, curlers are taken off before application of the oxidizing agent or the latest right after application of the oxidizing agent.

The reducing and/or oxidizing compositions used in the novel process of the present invention comprise a cross linked copolymer of vinylpyrrolidone, vinylimidazol, 3-methyl-1-vinylimidazolium chloride and methacrylic acid. Suitable and the most preferred polymer is Polyquaternium-86 and commercially available under the trade name Luvigel Advanced from BASF. Concentration of the cross linked copolymer is in the range of 0.01 to 10%, preferably 0.1 to 7.5, more preferably 0.2 to 5% and most preferably 0.5 to 5% by weight calculated to total of each composition.

It should be noted that throughout the description specified concentrations are all calculated to total of the respective composition, unless otherwise stated.

The reducing composition comprises at least one reducing compound. Preferred are thioglycolic acid and thiolactic acid as well as the salts thereof, in particular the ammonium and ethanolamine salts. Further useful thio compounds are in particular cysteine or the hydrochloride thereof, homocysteine, cysteamine, N-acetyl cysteine, thioglycerol, ethanediol monothioglycolate, 1,2-propyleneglycol monothioglycolate (see also WO-A 93/1791), 1,3-propanediol monothioglycolate or the isomer mixture resulting therefrom, 1,3-butanediol and 1,4-butanediol monothioglycolate and the isomer mixtures therefrom, polyethylene glycol, such as di-, tri- and tetraethyleneglycol monothioglycolates, glycerol monothiolactate and further thio acids and the esters thereof, as well as mixtures thereof.

The use of inorganic reducing sulfur compounds such as sodium hydrogen sulfite is principally also possible.

The total reduction agent content of the reducing compositions is in the range of 0.5 to 15%, preferably 1 to 15%, more preferably 2 to 12.5% and most preferably 2.5 to 12.5% by weight, calculated to total composition.

The composition comprising reducing agents can, if necessary, comprise alkalizing agents. Their quantity is dependent on the reducing agent and the desired pH-value of the composition. Reducing agent compositions preferably comprise alkalizing agent in a concentration range of 0.1 to 5%, in particular about 0.5% to about 2.5% by weight thereof, calculated to the total composition. Alkalizing agents preferred within the scope of the invention are ammonium carbamate, ammonia and/or ammonium(bi)carbonate, triethanolamine and monoethanolamine. It is desirable to adjust the pH-value between about 6.5 and 10.5, preferably about 7 to 9.5.

The viscosity best suited for the reducing compositions proved to be in the range of 500 to 10,000 mPa·s, preferably 1,000 to 5,000 mPa·s, measured at 20° C. in a Brookfield viscosimeter (no. 5 spindle), whereas the viscosity suited for the straightening compositions is preferably higher in a range up to about 50,000 mPa·s, preferably up to 30,000 mPa·s measured at 20° C. in a Brookfield viscosimeter (no. 5 spindle).

The second component used in the inventive process is a composition comprising at least one oxidizing agent. Suitable ones are such as hydrogen peroxide and sodium bromate. Most preferred is hydrogen peroxide. Oxidizing agent is comprised at a concentration of 0.05 to 15%, preferably 0.1 to 15% more preferably 0.25 to 12.5% and most preferably 0.5 to 10% by weight calculated to total composition. The oxidizing composition has a pH between 2 and 7, preferably 2.5 and 6 and more preferably 3 and 5.

Consistency of the oxidizing composition is in the range of 500 to 10,000 mPa·s, preferably 1,000 to 5,000 mPa·s, measured at 20° C. in a Brookfield viscosimeter (no. 5 spindle), whereas the viscosity suited for the straightening compositions is preferably higher in a range up to 50,000 mPa·s, preferably up to 30,000 mPa·s measured at 20° C. in a Brookfield viscosimeter (no. 5 spindle).

In a further preferred embodiment of the present invention, an intermediate treatment composition is applied onto hair after rinsing of the reducing composition and before applying the oxidizing composition. Still further preferred embodiment of the present invention is that intermediate composition is processed for up to 15 min, preferably up to 10 min and optionally rinsed off from hair prior to application of oxidizing composition.

Intermediate composition used in the inventive process of the present invention comprises further at least one inorganic salt, preferably at a concentration of 0.5 to 15%, more preferably 1 to 12.5% and most preferably 2 to 12.5% by weight calculated to total composition.

In principal any water soluble inorganic salt is suitable for the purpose of the present invention. In the preferred embodiment, salts are preferably selected from salts of mono or divalent cations with mono and divalent anions. Preferred cations are sodium, calcium, potassium and magnesium and anions are chloride and sulfate. Suitable ones are such as sodium chloride, sodium sulfate, magnesium sulfate, potassium chloride, potassium sulfate, magnesium chloride, calcium chloride, ammonium salts such as ammonium chloride and ammonium sulfate. Additionally it has been found to be suitable especially salts of iodide ions especially potassium and sodium salts, copper chloride, copper sulphate, cobalt chloride, cerium sulphate, cerium chloride, vanadium sulphate, lithium chloride, potassium dichromate, magnesium acetate, calcium nitrate, barium nitrate, magnesium oxide, and ammonium nitrate. Preferred inorganic salts are sodium chloride, sodium sulfate, magnesium sulfate, potassium chloride, potassium sulfate, magnesium chloride, calcium chloride and salts of iodide ions. More preferably the salts are sodium chloride, sodium sulfate, magnesium sulfate, potassium chloride, potassium sulfate, magnesium chloride and salts of iodide ions especially potassium and sodium salts. In particular, with magnesium sulfate, sodium chloride and potassium iodide exceptionally good results were observed.

Concentration of at least one inorganic salt in the aqueous composition is typically from 0.01 to 20%, preferably 0.05 to 15% and most preferably 0.1 to 10% and in particular 0.2 to 7.5% by weight calculated to the total composition. The concentration range disclose herein is the total concentration of the inorganic salts in case more then one is used in mixture.

Intermediate treatment composition comprises preferably at least one oxidizing agent at a concentration of 0.1 to 5%, preferably 0.2 to 5% more preferably 0.2 to 3% and most preferably 0.2 to 2% by weight calculated to total composition. Suitable oxidizing agents are such as hydrogen peroxide and sodium bromate. Most preferred is hydrogen peroxide.

In a further preferred embodiment of the present invention that intermediate treatment composition comprises as well a cross linked copolymer of vinylpyrrolidone, vinylimidazol, 3-methyl-1-vinylimidazolium chloride and methacrylic acid, preferably Polyquaternium-86 in concentration ranges given above for reducing composition.

The intermediate treatment composition has a pH between 2 and 7, preferably 2.5 and 6 and more preferably 3 and 5.

In a still further preferred embodiment of the present invention, prior to application of the reducing composition an aqueous pretreatment composition is applied onto hair comprising at least one inorganic salt. Still preferably the pretreatment composition is applied onto dry or wet or freshly shampooed hair and process optionally up to 20 min, preferably up to 15 min and more preferably up to 10 min and optionally rinsed off prior to application of reducing composition. The suitable and the preferred inorganic salts are same as the ones given above for the intermediate treatment composition in the same concentration ranges. Preferably, pretreatment composition comprises as well a cross linked copolymer of vinylpyrrolidone, vinylimidazol, 3-methyl-1-vinylimidazolium chloride and methacrylic acid, more preferably Polyquaternium-86. The concentration ranges given for the reducing composition above apply for the pretreatment composition as well. Viscosity of the pretreatment composition is up to 5000 mPa·s measured with either Höppler or Brookfield viscosimeter with the known means as explained in the manuals of the respective equipments at 20° C.

In principal pH of the aqueous pretreatment composition comprising at least one inorganic salt is not critical. However, preferably the pH of the composition must be chosen in a range which does not make any big changes in the pH of the reducing composition applied subsequently. Preferably the pH of the aqueous composition is in the range of 4 to 9, more preferably 5 to 8.5 and most preferably 6 to 8. Any of the aqueous compositions used in the inventive process of the present invention as disclosed above can comprise one or more of the following ingredients.

One or more of aqueous compositions may comprise additional thickening polymer of any kind, namely, anionic, cationic, nonionic and/or amphoteric polymers. Natural polymers such as chitosan and its derivatives, cellulose and its derivatives and hydroxyethylcellulose and guar gum and their derivatives may be comprised in any of the aqueous compositions used in the novel process of the present invention.

One or more of aqueous compositions may comprise cationic polymers as thickeners and at the same time conditioning agents which enhances first of all combability and therefore makes applications onto hair easier. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore. chitosan and chitin can also be included in the compositions as cationic natural polymers.

Furthermore, those cationic polymers known with their CTFA category name Polyquaternium may as well be added into pre-treatment compositions of the present invention. Typical examples of those are Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46, Polyquaternium 67, Polyquaternium 87.

The cationic polymers also include the quaternized products of graft polymers from organopolysiloxanes and polyethyl oxazolines described in EP-A 524 612 and EP-A 640 643.

Concentration of the polymers of anionic, cationic, non-ionic and/or amphoteric or zwitterionic character mentioned above is in the range of 0.05-10%, preferably 0.1-7.5%, preferably 0.2-7.5% and most preferably 0.2-5% by weight, calculated to the total composition.

One or more aqueous compositions of inorganic salt may comprise one or more surfactants selected from non-ionic, anionic, cationic and amphoteric ones.

The surfactants suitable for the compositions are nonionic surfactants. Preferred nonionic surfactants are ethoxylated fatty alcohols according to the following formula:

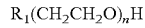

where $R_1$ is a saturated or unsaturated, linear or branched alkyl chain with 12 to 22 C atoms and n is a number between 2 and 50 preferably 2 to 40, more preferably 2 to 30. In one of the preferred embodiments of the invention, the hair treatment compositions comprise a mixture of two nonionic fatty alcohol ethoxylates, one has between 2 to 10 ethoxylate units and the other is more than 10. Those surfactants are known by the generic terms for example "Laureth", "Myristeth", "Oleth", "Ceteth", "Deceth", "Steareth" and "Ceteareth" according to the CTFA nomenclature, including addition of the number of ethylene oxide molecules. e.g. "Ceteareth-20", Steareth-2, Further nonionic surfactants suitable are those polyethylene glycol ethers of monogylcerides according to the general formula

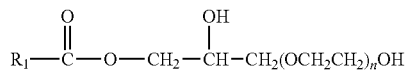

$R_1$ and n are same as above. Examples to those types of nonionic surfactants are PEG-7-glyceryl cocoate known with the trade name Cetiol HE from Cognis, PEG-8-glyceryl laurate know with the trade name Glycerox L8 from Croda Chemicals, PEG-10 glyceryl oleate, PEG-15 glycerryl isostearate, PEG-5 glycerryl stearate, PEG-15 gylceryl ricinoleate, etc.

Further nonionic surfactants suitable are alkyl polyglucosides of the general formula

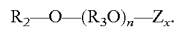

wherein $R_2$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

Additionally useful nonionic surfactants are the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Still further suitable nonionic surfactants are amineoxides. Such amineoxides are known especially because of their use in cleansing compositions, for example $C_{12}$-$C_{18}$-alkyl dimethyl aminoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain, Those are on the market, for example, under the trade names "Ammonyx®", "Aromox®" or "Genaminox®".

Anionic surfactants of the sulfate, sulfonate, carboxylate types are as well suitable in compositions of the present invention. Those are the ones very commonly used in cosmetic cleansing preparations, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof.

Additional anionic surfactants are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

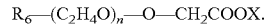

wherein $R_6$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

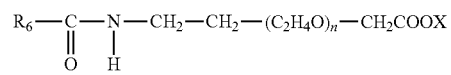

wherein $R_6$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in mixture with other anionic surfactants, as well as sulfofatty acids and the esters thereof.

It is also possible to use mixtures of several anionic surfactants in mixture within the scope of the invention.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

As further surfactant component, one or more of aqueous compositions may comprise amphoteric or zwitterionic surfactants.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Cationic surfactants may also be comprise in one or more aqueous compositions and particularly as conditioning agent and according to the general formula

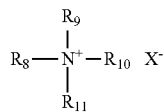

where $R_8$ is a saturated or unsaturated, branched or non-branched alkyl chain with 8-22 C atoms or

where $R_{12}$ is saturated or unsaturated, branched or non-branched alkyl chain with 7-21 C atoms and n has typical value of 0-4 or

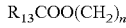

where $R_{13}$ is saturated or unsaturated, branched or non-branched alkyl chain with 7-21 C atoms and n has typical value of 0-4. and
$R_9$ is a lower alkyl chain with 1 to 4 carbon atoms, saturated or unsaturated, branched or non-branched alkyl chain with 8-22 C atoms or

where $R_{12}$ is saturated or unsaturated, branched or non-branched alkyl chain with 7-21 C atoms and n has typical value of 0-4 or

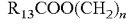

where $R_{13}$ is saturated or unsaturated, branched or non-branched alkyl chain with 7-21 C atoms and n has typical value of 0-4. and
$R_{10}$ and $R_{11}$ are independent from each other a lower alkyl chain with 1 to 4 carbon atoms, and X is chloride, bromide or methosulfate.

Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, dipalmitoyl dimonium chloride, distearyl dimethyl ammonium chloride, stearamidopropyl trimonuim chloride and dioleoylethyl dimethyl ammonium methosulfate, etc.

From the above quaternary ammonium compounds disclosed with the general formula, especially preferred as hair conditioning agents are those compounds known per se and are on the market, for example, under the trade names "Schercoquat®", "Dehyquart® F30" and "Tetranyl®".

Again from the above quaternary ammonium compounds disclosed with the general formula, especially preferred as conditioning ingredient are these compounds are known per se and on the market, for example, under the trade name "INCROQUAT® HO" or "OCS". Those compounds are known with a general ingredient category under "amidoquat" in the cosmetic industry.

According to present invention total concentration of surfactants of anionic, cationic, non-ionic and/or amphoteric or zwitterionic character is in the range of 0.05-10%, preferably 0.05-7.5% and most preferably 0.05-5% by weight, calculated to the total composition of each composition.

One or more of aqueous composition can also comprise conditioning agents selected from oily substances and non-ionic substances. Oily substances are selected from such as silicone oils volatile or non-volatile, natural and synthetic oils. Among silicone oils those can be added include dimethicone, dimethiconol, polydimethylsiloxane, DC fluid ranges from Dow Corning, arylated silicones, aminated silicones, natural oils such as olive oil, almond oil, avocado oil, wheatgerm oil, ricinus oil and the synthetic oils, such as mineral oil.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters.

Conditioners mentioned above can be contained at a concentration of below 1%, preferably below 0.75% by weight, calculated to total composition.

One or more of the aqueous compositions can comprise one or more organic solvent. Examples are such as ethanol. propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of one or more organic solvents is in the range of 1 to 25%, preferably 1 to 20%, more preferably 1 to 15% and most preferably 1 to 10% by weight, calculated to the total composition.

One or more of the compositions may comprise at least one ubiqinone of the formula

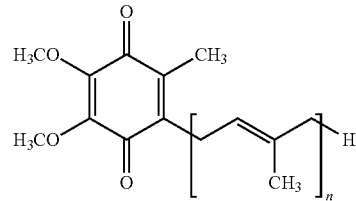

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total of each composition.

The compositions comprise ubiquinone which is preferably selected from the ones where n is a number between 6 and 10 and more preferably it is ubiquinone 50 where n is 10, also known as Coenzyme Q10.

One or more of the aqueous composition can comprise at least one amino acid. At least one amino acid is comprised at a concentration of 0.01 to 10%, preferably 0.05 to 7.5% and more preferably 0.1 to 5% and most preferably 0.25 to 5% by weight calculated to total of each composition.

Suitable amino acids are glycin, histidine, citrullin, asparagine, alanin, valin, leucin, isoleucin, pyrrolin, tryptophane, phenylalanine, methionine, serine, tyrosine, threonine and gluatamine. Preferably, the amino acid is selected from glycin, histidine, citrullin, asparagine, alanin, valin, leucin, isoleucin, pyrrolin, serine, tyrosine, threonine and gluatamine. More preferably, at least one amino acid is selected from glycin, histidine, asparagine, alanin, valin, leucin, pyrrolin, serine, tyrosine and gluatamine, and most preferably at least one amino acid is selected from glycin, asparagine, alanin, valin, leucin, and serine.

One or more of the aqueous composition can comprise further ceramide type of compound with the general formula

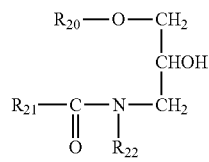

where $R_{20}$ and $R_{21}$ are independent from each other alkyl- or alkenyl group with 10 to 22 carbon atoms, $R_{22}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Further optional ingredient are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Optionally fatty acids of $C_{10}$ to $C_{22}$ may be incorporated into the compositions of the present invention at a concentration of preferably 0.01 to 2.5% by weight calculated to total of each composition.

In a further preferred embodiment of the present invention, One or more of the aqueous composition can comprise at least one diamine compound. Preferred diamide compounds are according to the general structure

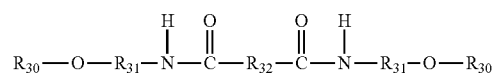

wherein $R_{30}$ is a linear or branched, saturated or unsaturated alkyl chain with 1 to 12 C atoms which may be substituted with hydroxy and/or alkoxy groups, preferably $R_{30}$ is linear or branched, saturated or unsaturated alkyl chain with 1 to 12 C atoms which may be substituted by 1 to 3 substituents selected from a hydroxy group and C1 to C6 alkoxy group, more preferably $R_{30}$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{31}$ is linear or branched alkyl chain with 1 to 5 C atoms, preferably linear or branched alkyl chain with 2 to 5 C atoms and more preferably an alkyl chain with 2 to 3 C atoms, and $R_{32}$ linear or branched, saturated or unsaturated alkyl chain with 1 to 22 C atoms, preferably linear or branched, saturated or unsaturated alkyl chain with 11 to 22 C atoms.

Preferred individual diamide compounds are the ones according to the formula A to G.

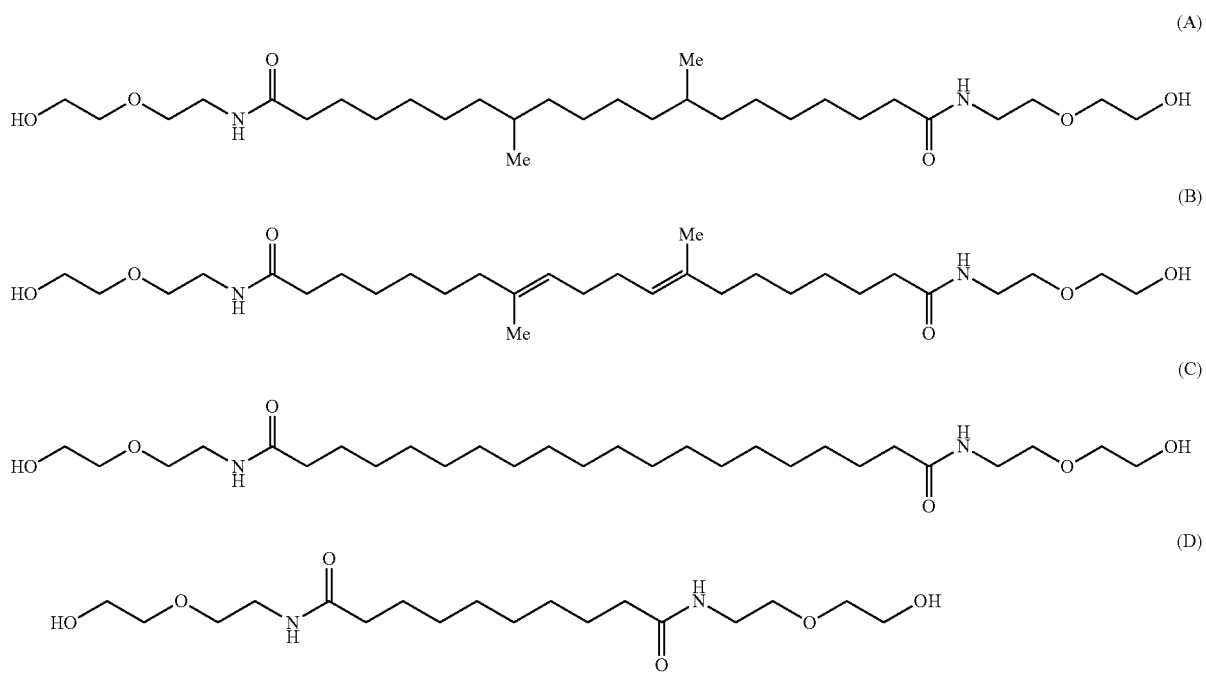

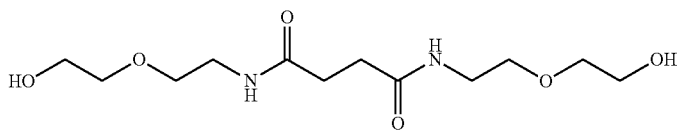
(E)

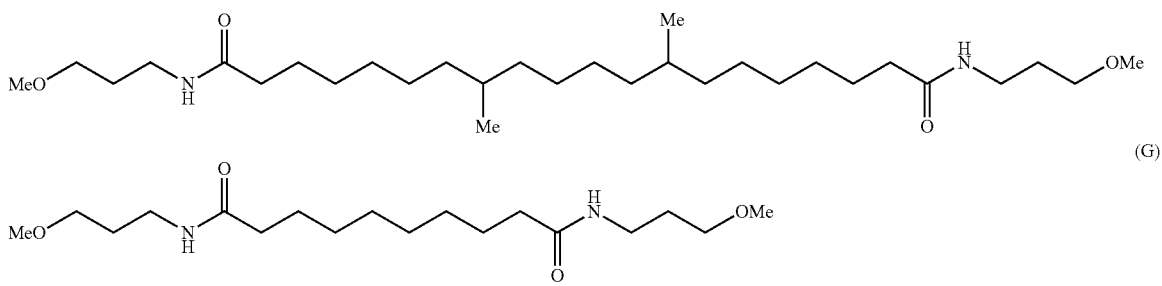
(F)

(G)

Particularly preferred diamide compound is the compound F which is bis (methoxypropylamido) isodocosane and commercially available from Kao Corporation—Japan.

Concentration of diamide compounds in the intermediate treatment compositions of the present invention is in the range of 0.001 to 5%, preferably 0.002 to 3% more preferably 0.005 to 2% and most preferably 0.01 to 1% by weight calculated to total of each composition.

Another preferred compound one or more of the aqueous compositions comprise silicone compounds and especially aminated silicones such as amodimethicone available from for example Dow Corning under the brand names Dow Corning 949 Emulsion and Dow Corning 2-8194 ME. Concentration of silicones, especially amodimethicone, is in the range of 0.05 to 2.5%, preferably 0.1 to 1% by weight calculated to total or each composition.

Additionally, one or more natural oil may be incorporated into the one or more of the aqueous compositions of the present invention. Suitable are such as olive oil, almond oil, avocado oil, wheatgerm oil, ricinus oil or their mixture. Concentration of these natural oil ingredients should be 0.01 to 2.5%, preferably 0.01. to 1%, more preferably 0.05 to 0.5% by weight, calculated to total each composition.

The compositions used according to the invention can naturally comprise all the substances customarily found in permanent shaping compositions, a list of which will not be given here, and are preferably present as solutions, gels with a higher or lower viscosity, emulsions or creams. They can be single-phase products or compositions packed into separate packaging which are united upon application, as they are disclosed, for example, in DE-C 43 04 828.

In order to avoid repetition, reference is here made to the state of the art as it is described, for example, in "Ullmann's Encyclopedia of Industrial Chemistry", Vol. A12 (1986), pages 588 to 591, and in particular to the monography of K. Schrader, "Grundlagen and Rezepturen der Kosmetika", $2^{nd}$. Ed. (1989, Hüthig Buchverlag) pages 823 to 840, as well as the article by D. Hollenberg et. al. in "Seifen-Öle-Fette-Wachse", 117 (1991), pages 81 to 87.

The compositions used in the inventive process of the present invention are preferably provided in a kit. Accordingly further objective of the present invention is a kit for permanent shaping keratin fibers preferably hair comprising
 a—optionally an aqueous composition comprising at least one organic salt,
 b—an aqueous composition comprising at least one reducing agent,
 c—an aqueous composition comprising at least one oxidizing agent, and
 d—optionally, another aqueous composition comprising at least one inorganic salt and optionally at least one oxidizing agent
with the condition that at least one of the above compositions, preferably composition b, more preferably compositions b and c comprise at least one a cross linked copolymer of vinylpyrrolidone, vinylimidazol, 3-methyl-1-vinylimidazolium chloride and methacrylic acid, preferably polyquaternium-86.

The following examples are to illustrate the invention, but not to limit it.

EXAMPLE 1

Alkaline Permanent Wave for Normal Hair

|  | % by weight |
| --- | --- |
| Ammonium thioglycolate (60%) | 21.3 |
| Ammonium hydrogen carbonate | 5.0 |
| 1,3-butylene gylcol | 3.0 |
| Amodimethicone | 0.2 |
| PEG-40-Hydrogenated castor oil | 0.7 |
| Luvigel Advanced | 0.5 |
| Perfume | 0.4 |
| Ammonia, 25% | ad pH 8.3 |
| Water | ad 100.0 |

Oxidizing Composition

|  | % by weight |
| --- | --- |
| Hydrogen peroxide | 2 |
| Phosphoric acid | q.s. to pH 3.5 |
| Water | to 100 |

With these compositions the hair was permanently waved according to the process of the present invention. Therefore, hair was shampooed and towel dried and hair was put on curlers and reducing composition given above was applied onto hair and processed for about 15 minutes, rinsed off from hair and oxidizing composition was applied and processed for about 10 minutes and rinsed off from hair and curlers were taken off from hair. Homogeneous wave appearance and natural hair feeling was obtained. It was observed that the application of reducing composition onto hair was much easier compared to a composition without Luvigel Advanced but with hydroxyethylcellulose. Furthermore, exclusion of the Luvigel Advanced resulted in less homogeneous perm appearance and especially natural hair feeling was lost.

EXAMPLE 2

Intermediate Composition

|  | % by weight |
| --- | --- |
| Coenzyme Q10 | 0.2 |
| Polysorbate-80 | 0.2 |
| Magnesium sulfate | 10 |
| Cetrimonium chloride | 0.5 |
| Citric acid | q.s. to pH 4.2 |
| Water | q.s. to 100 |

The two compositions used in Example 1 were used in this example. The permanent shaping was carried out as follows:

Hair was shampooed and towel dried and hair was put on curlers and reducing composition given above was applied onto hair and processed for about 15 minutes, rinsed off from hair and the intermediate composition of above was applied onto hair and after processing of 10 min and without rinsing off oxidizing composition was applied and immediately afterwards the curlers were taken off from hair and oxidizing composition was processed further for about 10 minutes and rinsed off from hair. Homogeneous wave appearance and natural feeling hair was obtained. Application of the above compositions was easy onto hair. Exclusion of Luvigel Advanced resulted in less homogeneous perm appearance and especially natural hair feeling was lost. It was furthermore observed that hair appear and feel less damaged.

EXAMPLE 3

Pretreatment Composition

|  | % by weight |
| --- | --- |
| Polysorbate-80 | 0.2 |
| Magnesium sulfate | 5 |
| Luvigel Advanced | 1.0 |
| Cetrimonium chloride | 1.0 |
| Arginine | 0.5 |
| Citric acid | q.s. to pH 4.2 |
| Water | q.s. to 100 |

Alkaline Permanent Wave for Damaged Hair

|  | % by weight |
| --- | --- |
| Ammonium thioglycolate (60%) | 0.9 |
| Cystein hydrochloride | 5.7 |
| Ammonium hydrogen carbonate | 1.5 |
| Acetylcystein | 0.7 |

-continued

|  | % by weight |
| --- | --- |
| Cetrimonium chloride | 0.1 |
| 1,3-butylene gylcol | 0.5 |
| Luvigel Advanced | 0.5 |
| Amodimethicone | 0.2 |
| Oleic acid | 0.05 |
| Perfume | 0.4 |
| Ammonia, 25% | ad pH 9.8 |
| Water | q.s. 100.0 |

Intermediate Composition

|  | % by weight |
| --- | --- |
| Polysorbate-80 | 0.2 |
| Magnesium sulfate | 10 |
| Hydrogen peroxide | 2.5 |
| Luvigel Advanced | 0.2 |
| Cetrimonium chloride | 1.0 |
| Arginine | 0.5 |
| Citric acid | q.s. to pH 4.2 |
| Water | q.s. to 100 |

Oxidizing composition of Example 1 was used.

The permanent wave achieved with the above compositions was homogeneous, natural in appearance and in touching. Exclusion of Luvigel Advanced resulted in less homogeneous curls and natural hair feeling upon touching was not observed.

EXAMPLE 4

Pretreatment Composition

|  | % by weight |
| --- | --- |
| Polysorbate-80 | 0.2 |
| Sodium chloride | 10 |
| Behentrimonium chloride | 0.8 |
| Arginine | 0.5 |
| Citric acid | q.s. to pH 4.2 |
| Water | q.s. to 100 |

Neutral Permanent Wave for Normal Hair

A permanent waving product consisting of two Compositions A and B, filled into a two-chamber packaging the chambers of which were kept separate until application, was prepared by destruction of the separating wall prior to application onto hair.

Composition A:

|  |  |
| --- | --- |
| Ammonium hydrogen carbonate | 4.5 (g) |
| Polyquaternium-6 | 1.0 |
| PEG-65-Hydrogenated castor oil | 0.8 |
| Isopropyl alcohol | 1.5 |
| Ethoxydiglycol | 2.0 |
| Cocoamidopropyl betaine | 1.0 |
| Luvigel Advanced | 1.0 |
| Perfume | 0.3 |
| Turbidifying agent | 0.5 |
| Ammonia, 25% | ad pH 8.4 |
| Water | q.s. 72.0 |

Composition B:

| | |
|---|---|
| Ammonium thioglycolate, 70% | 18.0 (g) |
| Thiolactic acid | 2.0 |
| 2-Methyl-1.3-propanediol | 0.5 |
| Ammonia, 25% | ad pH 5.5 |
| Water | q.s. 28.0 |

After admixture of both Compositions a ready-to-use product with a pH-value of 7.4 was obtained.
Intermediate Composition

| | % by weight |
|---|---|
| Polysorbate-80 | 0.2 |
| Sodium chloride | 10 |
| Hydrogen peroxide | 2.5 |
| Behentrimonium chloride | 0.8 |
| Arginine | 0.5 |
| Citric acid | q.s. to pH 4.2 |
| Water | q.s. to 100 |

Oxidizing composition of Example 1 was used.

With these compositions the hair was permanently waved. Therefore, hair was shampooed and towel dried and first aqueous composition was applied and processed for 5 min and hair was put on curlers and reducing composition given above after mixing the two parts, was applied onto hair and processed for about 20 minutes, rinsed off from hair and intermediate composition of above was applied onto hair and processed for 5 min and without rinsing off oxidizing composition was applied and processed for about 8 minutes and rinsed off from hair. Homogeneous wave appearance and natural feeling hair was obtained.

Exclusion of Luvigel Advanced from reducing composition resulted in less homogeneous perm appearance. Additionally, the compositions were applied onto hair much easier than known with other comparable compositions.

EXAMPLE 5

First Aqueous Composition

| | % by weight |
|---|---|
| PEG-60 Hydrogenated castor oil | 0.2 |
| Sodium chloride | 10 |
| Luvigel Advanced | 1.5 |
| Cetrimonium chloride | 0.5 |
| Arginine | 0.5 |
| Citric acid/sodium hydroxide | q.s. to pH 6.5 |
| Water | q.s. to 100 |

Neutral Permanent Wave for Dyed Hair

A permanent waving product filled into a two-chamber package was prepared in analogy to Example 4:
Composition A:

| | |
|---|---|
| Ammonium hydrogen carbonate | 3.5 (g) |
| Polyquaternium-11 | 0.5 |
| Luvigel Advanced | 4.0 |
| 1-Methoxypropanol | 1.5 |
| Cocoamidopropyl betaine | 1.0 |
| PEG-25-glyceryl cocoate | 0.8 |
| Oleic acid | 0.05 |
| Perfume | 0.3 |

| | |
|---|---|
| Turbidifying agent | 0.5 |
| Ammonia, 25% | ad pH 8.3 |
| Water | q.s. 72.0 |

Composition B:

| | |
|---|---|
| Ammonium thioglycolate, 70% | 13.0 (g) |
| Thiolactic acid | 0.5 |
| 2-Methyl-1.3-propanediol | 1.5 |
| Ammonia, 25% | ad pH 5.5 |
| Water | q.s. 28.0 |

A product with a pH-value of 7.4 was obtained by admixture of the Compositions immediately prior to application.
Intermediate Composition

| | % by weight |
|---|---|
| Coenzyme Q10 | 0.1 |
| PEG-60 Hydrogenated castor oil | 0.2 |
| Sodium chloride | 10 |
| Hydrogen peroxide | 2.5 |
| Cetrimonium chloride | 0.5 |
| Luvigel Advanced | 0.7 |
| Arginine | 0.5 |
| Citric acid | q.s. to pH 4.2 |
| Water | q.s. to 100 |

Oxidizing composition of example 1 with 0.2% Luvigel Advanced was used. Homogeneous and natural appearing curls were obtained. Exclusion of Luvigel Advanced resulted in loss of effects.

EXAMPLE 6

First Aqueous Composition

| | |
|---|---|
| Asparagic acid | 0.25% by weight |
| Glutamic acid | 0.50 |
| Alanin DL | 0.25 |
| Behentrimonium chloride | 1.00 |
| Luvigel Advanced | 0.25 |
| Potassium iodide | 5.00 |
| Polysorbate-80 | 0.10 |
| Coenzyme Q10 | 0.05 |
| Citric acid/sodium hydroxide | q.s to pH 6.8 |
| Water | q.s. to 100 |

The above composition had a pH of 4.10.
Alkaline Permanent Waving Gel

| | |
|---|---|
| Ammonium thioglycolate, 70% | 15.0 (g) |
| Ammonium hydrogen carbonate | 4.5 |
| PEG-40-Hydrogenated castor oil | 0.7 |
| $C_{12}$-$C_{18}$-Fatty alcohol mixture | 3.5 |
| Cetrimonium chloride | 2.0 |
| Amodimethicone | 0.05 |
| 2-Methyl-1.3-propanediol | 0.5 |
| Polyquaternium-28 | 0.1 |
| Luvigel Advanced | 1.5 |
| Perfume | 0.3 |
| Ammonia, 25% | ad pH 8.0 |
| Water | q.s. 100.0 |

Intermediate Treatment Composition

| | |
|---|---|
| Asparagic acid | 0.25% by weight |
| Glutamic acid | 0.50 |
| Alanin DL | 0.25 |
| Behentrimonium chloride | 1.00 |
| Luvigel Advanced | 0.50 |
| Hydrogen peroxide | 1.50 |
| Magnesium sulfate | 10.00 |
| Polysorbate-80 | 0.10 |
| Coenzyme Q10 | 0.05 |
| Water | q.s. to 100 |

The above composition had a pH of 4.10.

Oxidizing composition of example 1 with 0.2% Luvigel Advanced was used. Homogeneous and natural appearing curls were obtained. Exclusion of Luvigel Advanced resulted in loss of effects.

EXAMPLE 7

Straightening Composition

| | |
|---|---|
| Thioglycolic acid | 8.0 (% by wt.) |
| $C_{16}$-$C_{22}$-Fatty alcohol mixture | 3.5 |
| Oleth-50 | 2.5 |
| Luvigel Advanced | 1.0 |
| Laureth-23 | 1.5 |
| Polyquaternium-2 | 0.8 |
| Oleic acid | 0.1 |
| Ethanol | 5.0 |
| Perfume | 0.6 |
| Monoethanolamine | ad pH 9.3 |
| Water | q.s. 100.0 |

Intermediate Composition

| | % by weight |
|---|---|
| Poysorbate-80 | 0.1 |
| Sodium chloride | 10 |
| Luvigel Advanced | 2.0 |
| Hydrogen peroxide | 2.5 |
| Cetrimonium chloride | 0.8 |
| Arginine | 0.5 |
| Citric acid | q.s. to pH 4.2 |
| Water | q.s. to 100 |

Kinky hair was straightened according to process wherein hair was shampooed and first aqueous composition of example 1 was applied onto hair and after processing of 10 min at ambient temperature, the above reducing composition was applied onto hair and processed for 20 min at ambient temperature and rinsed off from hair and hair was towel dried and treated with the above intermediate composition and without rinsing off hair was dried. Subsequently hair was straightened with a hot iron having flat shape and a temperature of approximately 140° C. and afterwards treated with an oxidizing composition comprising 2% by weight of hydrogen peroxide and 0.5% Luvigel Advanced at pH 3. Finally hair was rinsed off and dried with a drier. Hair was excellently straightened and felt natural and soft upon touching. Exclusion of Luvigel Advanced resulted in loss of effects. Compositions were applied onto hair easily.

The invention claimed is:

1. A process for permanent shaping hair, wherein the process comprises:
   (i) shampooing the hair;
   (ii) applying a reducing composition onto the hair, wherein the reducing composition has a pH between 8.0 and 10.5 and comprises at least one reducing agent present at a concentration from 0.5 to 15% by weight, calculated to the total of the reducing composition, wherein the at least one reducing agent is selected from group consisting of thioglycolic acid, thioglycolic acid ammonium salt, thiolactic acid, thiolactic acid salt, cysteine, cystein hydrochloride, homocysteine, cysteamine, N-acetyl cysteine, thioglycerol, ethanediol monothioglycolate, 1,2-propyleneglycol monothioglycolate, 1,3-propanediol monothioglycolate, 1,3-propanediol monothioglycolate isomer mixture, 1,3-butanediol monothioglycolate, 1,3-butanediol monothioglycolate isomer mixture, 1,4-butanediol monothioglycolate, 1,4-butanediol monothioglycolateisomer mixture, polyethylene glycol, thio acid, thio acid ester, and mixtures thereof;
   (iii) rinsing the reducing composition off from the hair after a processing time of 1 to 30 min and at a temperature of 20 to 45° C.;
   (iv) applying an oxidizing composition onto the hair and processing for 1 to 20 min at a temperature range of 20 to 45° C., wherein the oxidizing composition has a pH between 2 and 7 and comprises at least one oxidizing agent present at a concentration from 0.05 to 15% by weight, calculated to total of the oxidizing composition, wherein the at least one oxidizing agent is hydrogen peroxide or sodium bromate; and
   (v) rinsing the oxidizing composition off from the hair, wherein the reducing composition comprises Polyquaternium-86 at a concentration of 0.01 to 10% by weight, calculated to the total of the reducing composition.

2. The process according to claim 1, wherein both the reducing composition and the oxidizing composition comprise Polyquaternium-86.

3. The process according to claim 1, wherein Polyquaternium-86 is present at a concentration of 0.2 to 5% by weight, calculated to the total of the reducing composition.

4. The process according to claim 1, wherein the hair is put on curlers prior to application of the reducing composition comprising the at least one reducing agent.

5. The process according claim 4, wherein the curlers are removed from the hair after application of the oxidizing composition or at the end of the processing time of the oxidizing composition.

6. The process according to claim 1, wherein the reducing composition comprises the at least one reducing agent at a concentration of 1 to 15% by weight, calculated to the total of the reducing composition.

7. The process according to claim 1, wherein the reducing composition comprises at least one alkalizing agent and has a pH between 8.0 and 9.5 and the oxidizing composition has a pH between 3 and 5.

8. The process according to claim 1, wherein prior to application of reducing composition, a pretreatment composition is applied onto the hair and processed up to 20 min and optionally rinsed off from hair, wherein the pretreatment composition comprises at least one inorganic salt selected from magnesium sulfate, sodium chloride and potassium iodide and is present at a concentration of 0.01 to 20% by weight, calculated to the total of the pretreatment composition, further wherein the pretreatment composition, optionally, comprises Polyquaternium-86.

9. The process according to claim 1, wherein after rinsing off the reducing composition from hair, an intermediate treatment composition is applied onto hair and processed up to 10 min and optionally rinsed off from the hair, wherein the intermediate treatment composition comprises at least one inorganic salt selected from magnesium sulfate, sodium chloride and potassium iodide and is present at a concentration of 0.01 to 20% by weight, calculated to total of the intermediate composition, further wherein the intermediate treatment composition, optionally, comprises at least one oxidizing agent or Polyquaternium-86.

10. The process according to claim 1, wherein the reducing composition and/or the oxidizing composition comprises at least one organic solvent.

11. The process according to claim 1, wherein the reducing composition and/or the oxidizing composition further comprises one or more of the compounds selected from
surfactants,
conditioning agents,
ubiqinones of the formula

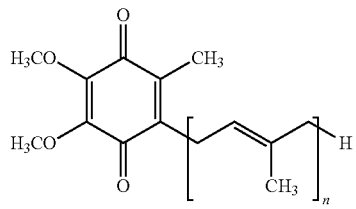

where n is a number between 1 and 10,
amino acid,
ceramide compound according to general formula

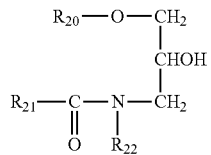

where $R_{20}$ and $R_{21}$ are independent from each other alkyl- or alkenyl group with 10 to 22 carbon atoms, $R_{22}$ is alkyl or hydroxyl alkyl with 1 to 4 carbon atoms group and n is a number between 1 to 6,
sterol,
diamide compounds according to general structure

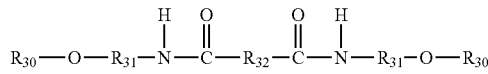

wherein $R_{30}$ is a linear or branched, saturated or unsaturated alkyl chain with 1 to 12 carbon atoms which may be substituted with hydroxy and/or alkoxy groups, $R_{31}$ is linear or branched alkyl chain with 1 to 5 carbon atoms, and $R_{32}$ linear or branched, saturated or unsaturated alkyl chain with 1 to 22 carbon atoms,
silicone compound, and
natural oil.

12. The process according to claim 8, wherein the pretreatment composition further comprises Polysorbate-80.

13. The process according to claim 9, wherein the intermediate treatment composition further comprises Polysorbate-80.

14. A process for permanent shaping hair, wherein the process comprises:
(i) shampooing the hair;
(ii) applying a reducing composition onto the hair, wherein the reducing composition has a pH between 8.0 and 9.5 and comprises at least one reducing agent present at a concentration from 2.5 to 12.5% by weight calculated to the total of the reducing composition, wherein the at least one reducing agent is selected from group consisting of ammonium thioglycolate, acetylcysteine, thiolactic acid and thioglycolic acid;
(iii) rinsing the reducing composition off from the hair after a processing time of 1 to 30 min and at a temperature of 20 to 45° C.;
(iv) applying an oxidizing composition onto the hair and processing for 1 to 20 min at a temperature range of 20 to 45° C., wherein the oxidizing composition has a pH between 2.5 and 6 and comprises an oxidizing agent present at a concentration of 0.5 to 10% by weight, calculated to the total of the oxidizing composition, wherein the oxidizing agent is hydrogen peroxide; and
(v) rinsing the oxidizing composition off from the hair, wherein the reducing composition comprises Polyquaternium-86 at a concentration of 0.2 to 5% by weight, calculated to the total of the reducing composition.

15. The process according to claim 14, wherein the reducing composition consists of the at least one reducing agent and the at least one reducing agent consists of ammonium thioglycolate present at a concentration of 10.5 to 12.5% by weight, calculated to the total of the reducing composition, wherein the oxidizing agent is present at a concentration of 2 to 10% by weight, calculated to the total oxidizing composition, and further wherein the reducing composition comprises the Polyquaternium-86 at a concentration of 0.2 to 0.5% by weight, calculated to the total of the reducing composition.

16. The process according to claim 15, wherein the reducing composition was rinsed off from the hair after the processing time of about 15 minutes and the oxidizing composition was rinsed off from the hair after a processing time of about 8 minutes, and further wherein the reducing composition has a pH of 8.3 to 9.5.

* * * * *